United States Patent [19]

Sustmann et al.

[11] Patent Number: 4,634,439

[45] Date of Patent: Jan. 6, 1987

[54] PH-REGULATING CELLULOSE FIBER

[75] Inventors: Scarlet Sustmann, Viersen, Fed. Rep. of Germany; Ingo G. Marini, Lenzing, Austria

[73] Assignee: Lenzing Aktiengesellschaft, Lenzing, Austria

[21] Appl. No.: 660,338

[22] Filed: Oct. 12, 1984

[30] Foreign Application Priority Data

Oct. 14, 1983 [DE] Fed. Rep. of Germany ....... 3337443

[51] Int. Cl.$^4$ .......................... B01J 20/28; B01J 20/24; B01J 20/30; D01F 11/02
[52] U.S. Cl. ..................................... 604/376; 536/87; 536/89; 106/169
[58] Field of Search ................... 604/376; 536/87, 88, 536/89; 106/169

[56] References Cited

U.S. PATENT DOCUMENTS

| | | | |
|---|---|---|---|
| 3,067,745 | 12/1962 | Burgeni et al. | 604/376 |
| 3,187,747 | 6/1965 | Burgeni | 128/156 |
| 4,044,766 | 8/1977 | Kaczmarzyk et al. | 128/283 |
| 4,405,324 | 9/1983 | Cruz, Jr. | 604/376 |
| 4,431,427 | 2/1984 | Lefren et al. | 604/285 |

Primary Examiner—Harold D. Anderson
Assistant Examiner—Nathan M. Nutter
Attorney, Agent, or Firm—Ernest G. Szoke; Mark A. Greenfield

[57] ABSTRACT

A cellulose fiber which is carboxyalkylated in free acid form, a fiber mass formed therefrom, and a method for producing such fiber.

18 Claims, No Drawings

PH-REGULATING CELLULOSE FIBER

BACKGROUND OF THE INVENTION

1. Field of the Invention

This invention relates to chemically modified fibers and their use as a pH-regulating material.

2. Statement of the Related Art

Absorbent materials, particularly those for medical, hygienic, cosmetic, or similar personal use, usually consist of hydrophilic cotton linters (i.e. absorbent cotton), viscose fibers, flexible foams, or the like.

Where such materials come into direct contact with parts of the body, it is advantageous to provide them with additives which positively affect the pH of the body at the point of contact, particularly by lowering or maintaining it. This assists in preventing irritation and reduces susceptibility to diseases, particularly those caused by alkaliphilic microorganisms.

An example of a known material of this type is disclosed in German Patent Application No. 23 09 575 which proposes impregnating tampons with substances which maintain a vaginal acid pH, such as glycogen, sugar, Doederlein bacteria, all of which help form lactic acid through *Lactobacillus acidophilus*. However, additives such as the above are not effective for their intended purpose, since the alkaline environment of the vagina during menstruation seriously inhibits the growth of *L. acidophilus*.

It has also been proposed in German Patent Application No. 23 09 575 (above) to impregnate with lactic acid per se, as well as citric acid, and the like. However, because of the strong buffer effect of menstrual fluid, and because of the relatively small amount of acid with which a tampon may be impregnated, the beneficial effect of the impregnant is exhausted after only a small accumulation of menstrual blood.

U.S. Pat. No. 4,431,427 and corresponding German Patent Application No. 32 36 768 describe tampons containing one or more substances which, when the tampon is in use, produce and maintain a pH in the range 2.5 to 4.5 and thus prevent the growth of pathogenic bacteria. Substances of the type in question are disclosed as including monomeric and/or polymeric, physiologically compatible carboxylic acids, such as citric acid, malic acid, tartaric acid or lactic acid. Tampons of this type also have the disadvantage that the strong buffer effect of the body fluids limits the acidifying effect of the acids introduced into the tampon.

U.S. Pat. No. 3,187,747 describes absorbing fiber materials having ion-exchange properties where the composition is a multicomponent polymer system. Polymer components having fiber-forming properties, for example textile fibers, are present alongside other polymers having acidifying properties, for example carboxymethyl cellulose, in the form of "polymer alloys" which may be obtained from homogeneous solutions of suitable polymers. The heterogeneity of the starting polymers means 30 that the processing of the polymer alloys into the required hygiene aids involves additional process steps, such as solvent exchange drying, in order to degelatinize the fibers and to prevent them from sticking to one another during the drying process. In addition, fibers of the type in question are frequently treated with cation-active softeners and lubricants to improve their processing properties, although this adversely affects the acidifying properties of the fiber material.

Another process in which a known material, a modified viscose fiber, is blended with a substance which, in use, produces a reduction in the pH is described in U.S. Pat. No. 4,044,766 and corresponding German Patent Application No. 27 09 132. Cellulose fibers are reacted with monochloroacetic acid to form carboxymethyl cellulose. The resulting carboxymethyl cellulose fibers have an average degree of substitution of from 0.4 to 2.0. This etherification process is carried out on the "finished" fiber. The disadvantage of this known process is that the subsequent etherification step yields fibers having a slimy surface which are unsuitable for medical, cosmetic, or similar applications. In addition, materials produced from fibers of this type only contain free carboxyl groups at the fiber surface, with the result that cationic substances present in body fluids bring about a rapid and complete deactivation of the pH-regulating capabilities of the fiber.

DESCRIPTION OF THE INVENTION

This invention affords a homogeneous cellulose fiber which has been modified in such manner as to be particularly effective as an acidic pH-regulating material. Most importantly, the inventive material demonstrates hardly any difference from conventional, unmodified fibers, both in its processing properties and in its service properties. For example, the inventive material has a high absorption capacity which makes it suitable for all normal absorbent cotton uses in addition to its highly desirable pH-regulating property.

The modified carboxyalkylated fibers of this invention are characterized by a degree of substitution of about 0.01 to 0.3, preferably about 0.07 to 0.1, which corresponds to about 1 to 30 (preferably about 7 to 10) carboxyalkyl groups per 100 anhydroglucose units, wherein substantially all of the carboxyalkyl groups are in the free acid form. Most importantly, the carboxyalkyl groups are distributed throughout the fiber, as contrasted with prior art fibers in which the substituted groups are mostly on the fiber surface. It is believed that this distribution of the carboxyalkyl groups makes the inventive material particularly effective for reasons that will be discussed below.

The alkyl moiety may have 1 to 3 carbon atoms, methyl being preferred. When the alkyl is methyl, the carboxyalkyl group content (COOH % by weight) of the cellulose fiber should be about 1.9 to 2.7% by weight, most preferably about 2% by weight, of the total fiber weight. This may be contrasted with a normal viscose fiber, which would contain about 0.3% by weight of carboxyl groups. The percentage will be fractionally lower if the alkyl has more than 1 carbon atom.

As a result of the coupled free acid moieties, fibers according to this invention have a pH of about between 3 and 4, most preferably about 3.4 to 3.9, when determined by Deutsche Industrienorm (DIN) 54,275. They will maintain in use a pH below about 6, preferably about 4 to 5. The pH may vary depending upon the degree of carboxyalkyl substitution and may be considered as an independent measurement of the number of free acid groups in the fiber.

The modified cellulose fibers of this invention are preferably prepared by first etherifying the cellulose polymer in a known manner, second preparing fibers from the etherified (i.e. carboxyalkylated) polymer mass, and third converting the alkalized carboxyalkyl fibers so that substantially all carboxy groups are in their free acid form, i.e. the carboxyalkyl groups consist essentially of carboxyalkyl groups in the free acid form. This sequence should be contrasted with the prior art process in which the fiber is first formed and then etherified [see comments regarding U.S. Pat. No. 4,044,766, above], which results in free carboxyl groups only at the fiber surface.

Carboxyalkylated cellulose fibers are already known, in which the carboxylation takes place before the fiber is formed. Such fibers are available, among others, from Chemiefaser Lenzing AG under the VISCOSORB trademark. In particular, fiber masses identified as VISCOSORB 1S and VISCOSORB 1N, are most useful for the purposes of this invention.

According to the inventive process, fibers which were carboxylated prior to fiber forming are treated with at least one aqueous mineral acid at room temperature for a period of about 20 to 40 (preferably about 30) minutes. All acid that has not reacted with the carboxyalkyl groups to convert them to free acid form is then thoroughly removed.

The aqueous mineral acid may be dilute hydrochloric, sulfuric, or the like. Aqueous hydrochloric acid in a concentration of about 0.1 to 1% by weight (preferably about 0.2% by weight) is particularly useful.

The removal of all unreacted acid is particularly important, and may be accomplished by at least one cycle of washing with deionized water and expressing most of the water, ultimately followed by drying, preferably at a temperature of about 90° to 115° C., most preferably about 100° to 105° C.

It has been noted that the acidification treatment in the preferred inventive process is conducted after the fiber has been formed.

The inventive fibers have a number of advantages over conventional, superabsorbent cotton wool.

Because of the low degree of substitution after conversion of the carboxylate group into the free acid form, the absorption capacity and absorption power of the materials according to the invention correspond to those of normal raw or regenerated cellulose or cotton.

Since the modification, i.e. etherification, is carried out on the actual cellulose raw material before production of the fiber, so that the free carboxyl groups are distributed throughout the fiber cross-section, the pH-regulating materials according to the invention have a distinctly better buffer capacity than materials modified after production of the fiber. They are thus able not only to establish, but importantly also to maintain an acidic pH.

There are no additional process steps, (such as solvent exchange drying), necessitated by a fiber material consisting of two or more polymer components. The modified pH-regulating materials show the properties indicated in the following examples without the addition of any other components, such as softeners or lubricants. Accordingly, the disadvantages normally produced by additions of components such as these do not arise.

The described materials according to the invention have many uses and are suitable for the production of sweat pads or shoe insoles, for cosmetic absorbent cotton and pharmaceutical bandaging, as well as for catamenial devices.

The invention is illustrated by the following examples.

EXAMPLE 1

Production of acidic fiber mass and determination of the fiber pH.

The fiber masses for the pH-regulating materials according to the invention were produced by converting the carboxylate groups of commercially available alkalized carboxyalkyl cellulose produced from carboxylalkylated cellulose by the viscose process into the free acid form. Fiber masses in 1 kg quantity were treated for 30 minutes at room temperature with 20 liters of 0.2% hydrochloric acid. The material was then squeezed out to a moisture content of 200% and washed with fully deionized water until the washing water showed a neutral reaction. It was then squeezed out again to a moisture content of approximately 200% and dried for 4 hours at 105° C. in a recirculating air drying cabinet. Determination of the fiber pH by the extrapolation process according to DIN 54 275 produced the results listed in Table 1.

TABLE 1

| Determination of the fiber pH in accordance with DIN 54 275. | | |
|---|---|---|
| Fiber material | Carboxyl groups | Fiber pH |
| VISCOSORB 1N* | 1.9% by weight | 3.4 |
| VISCOSORB 1S* | 2.7% by weight | 3.0 |
| Normal viscose | 0.3% by weight | 6.5 |

*modified according to this invention

EXAMPLE 2

Liquid retention capacity using water and blood serum as the test liquids.

Determination of the liquid retention capacity of the materials according to the invention was carried out with water in accordance with DIN 53 814 and with blood serum by the same method, but without the addition of wetting agents. The results are set out in Table 2 below.

TABLE 2

| Liquid retention capacity according to DIN 53 814. | | |
|---|---|---|
| Fiber Mass (% moisture after conditioning at 20° C./65% relative air humidity) | Retention capacity for: | |
| | Water (%) | Serum (%) |
| DANUFIL - a Hoechst product (14.3) | 65.2 | 70.1 |
| VISCOSORB 1N* - a Chemifaser Lenzing product (17.8) | 54.3 | 69.6 |
| VISCOSORB 1S* - a Chemifaser Lenzing product (16.9) | 53.3 | 70.9 |

*modified according to this invention

As can be seen, in the test carried out with blood serum, no differences were observed between the various materials. With water as the test liquid, the materials according to the invention show a slightly lower, but completely acceptable, retention capacity.

EXAMPLE 3

In vitro test for influencing the pH of blood serum by the materials according to the invention.

Quantities of 3.0 g of various fiber masses were added to quantities of from 10 to 30 ml of blood serum (pH 8.2.). The fiber mass samples had been treated as described in DIN 54 275. After a contact time of 60 minutes, the supernatant test liquid was centrifuged off from the sample and the pH determined using a commercially available pH-meter with a glass electrode. The effect of acidic fiber mass on the pH by comparison with normal viscose is shown in Table 3.

TABLE 3

Determination of the pH in accordance with DIN 54,275.

| Fiber Mass (3.0 g) (denier/staple length) | Serum pH for: (ml serum added) | | |
|---|---|---|---|
| | 10 ml | 15 ml | 30 ml |
| None added | 8.2 | 8.2 | 8.2 |
| Normal rayon (3.6 dtex/30 mm) | 7.88 | 8.04 | 8.17 |
| VISCOSORB 1S* (3.3 dtex/40 mm) | 4.09 | 4.30 | 4.96 |
| VISCOSORB 1N* (3.6 dtex/30 mm) | 4.30 | 4.50 | 5.44 |

*modified according to this invention

RESULTS

Even with 30 ml of blood serum on 3 g of fiber mass, the alkalinity of the serum can be neutralized and the pH kept near the physiological range. This demonstrates the utility of the modified fibers of this invention for topical cosmetic and pharmaceutical purposes including absorbent cotton, swabs, bandages, catamenial devices, and the like.

We claim:

1. Carboxy-$C_{1-3}$-alkyl cellulose homogenuous fiber wherein about 1 to 30 carboxyalkyl groups are present per 100 anhydroglucose units and wherein the carboxyalkyl groups consist essentially of carboxyalkyl groups in the free acid form, said carboxyalkyl groups being distributed throughout the length and diameter of the fiber.

2. The fiber of claim 1 wherein the alkyl is methyl.

3. The fiber of claim 2 wherein the carboxyalkyl group content of the fiber is about 1.9 to 2.7% by weight.

4. The fiber of claim 2 wherein the carboxyalkyl group content of the fiber is about 2% by weight.

5. The fiber of claim 1 wherein said fiber has, and will maintain in use, a pH of below about 6.

6. The fiber of claim 1 wherein said fiber has, and will maintain in use, a pH of about 3 to 4.

7. The fiber of claim 2 wherein said fiber has, and will maintain in use, a pH of about 3 to 4.

8. The fiber of claim 1 wherein said fiber has, and will maintain in use, a pH of about 3.4 to 3.9.

9. The fiber of claim 2 wherein said fiber has, and will maintain in use, a pH of about 3.4 to 3.9.

10. A method of producing pH-regulating fiber comprising:
carboxy-$C_{1-3}$-alkylating non-fibruous cellulose until about 1–30% of the cellulose anhydroglucose groups are carboxyalkylated;
forming fiber from said carboxyalkylated cellulose; and
treating the carboxyalkyl groups throughout the fiber with an aqueous mineral acid for a sufficient period of time to convert said carboxyalkyl groups to carboxyalkyl groups which consist essentially of carboxyalkyl groups in the free acid form.

11. The method of claim 10 wherein said treating step comprises thoroughly exposing carboxyalkylated fiber to a dilute aqueous mineral acid solution for about 20 to 40 minutes at ambient temperature, removing the fiber, thoroughly removing any acid solution remaining, and drying the fiber.

12. The method of claim 11 wherein the fiber is in the form of a fiber mass, treatment is by immersing the fiber mass in the aqueous mineral acid solution, and the acid solution is thereafter removed by at least one cycle of washing the fiber mass with substantially deionized water and expressing the wash water, followed by heat drying at about 90° to 115° C.

13. The method of claim 10 wherein the mineral acid is hydrochloric acid aqueous solution.

14. The method of claim 11 wherein the mineral acid is hydrochloric acid aqueous solution.

15. The method of claim 12 wherein the mineral acid is aqueous hydrochloric acid in a concentration of about 0.1 to 1% by weight.

16. The method of claim 12 wherein the mineral acid is aqueous hydrochloric acid in a concentration of about 0.2% by weight.

17. The method of claim 11 wherein the treating step is for about 30 minutes.

18. The method of claim 12 wherein the heat drying is at about 100° to 105° C.

* * * * *